United States Patent [19]

Owen

[11] 4,007,740
[45] Feb. 15, 1977

[54] CANNULA COVER
[75] Inventor: Robert A. Owen, Mount Prospect, Ill.
[73] Assignee: Illinois Tool Works Inc., Chicago, Ill.
[22] Filed: Feb. 11, 1976
[21] Appl. No.: 657,000
[52] U.S. Cl. .......................... 128/221; 128/218 N
[51] Int. Cl.² ........................................ A61M 5/00
[58] Field of Search ............ 128/221, 220, 218 P, 128/218 R, 218 N, 218 D, 215, 216

[56] References Cited
UNITED STATES PATENTS

| | | | |
|---|---|---|---|
| 2,833,281 | 5/1958 | Krug | 128/221 |
| 2,954,029 | 9/1960 | Metten | 128/218 D |
| 2,959,170 | 11/1960 | Laub | 128/218 P |
| 3,021,942 | 2/1962 | Hamilton | 128/221 X |
| 3,064,648 | 11/1962 | Bujan | 128/221 X |
| 3,073,307 | 1/1963 | Stevens | 128/221 |
| 3,185,150 | 5/1965 | Sorenson | 128/221 X |
| 3,294,231 | 12/1966 | Vanderbeck | 128/221 X |
| 3,304,934 | 2/1967 | Bautista | 128/221 X |

Primary Examiner—John D. Yasko
Attorney, Agent, or Firm—Jack R. Halvorsen; Robert W. Beart

[57] ABSTRACT

A tamper-proof, hermetically sealed cover for a cannula having a sharpened distal end. The cover is initially tubular encircling and covering a substantial portion of the cannula length and extending outwardly beyond the distal end. The free end of the cover is flattened and formed to provide a bubble-like chamber spaced in all directions from the sharpened distal end to avoid damage to the sharpened end; to hermetically seal the end for aseptic conditions and to prevent tampering if the cannula connects to a medicament source.

17 Claims, 12 Drawing Figures

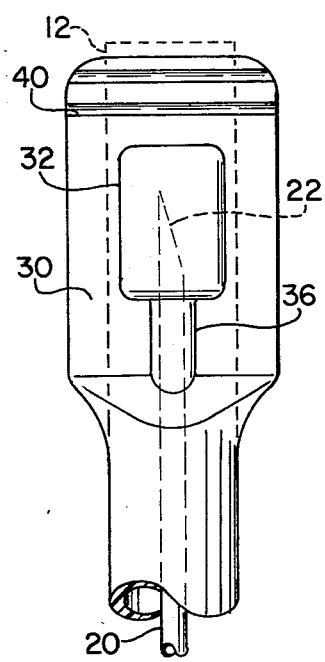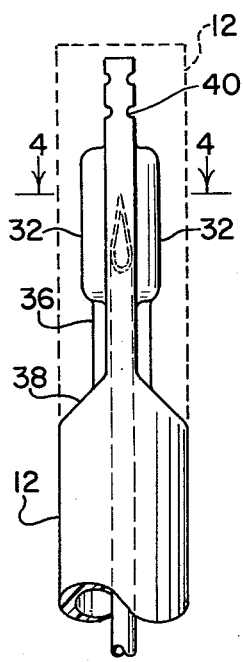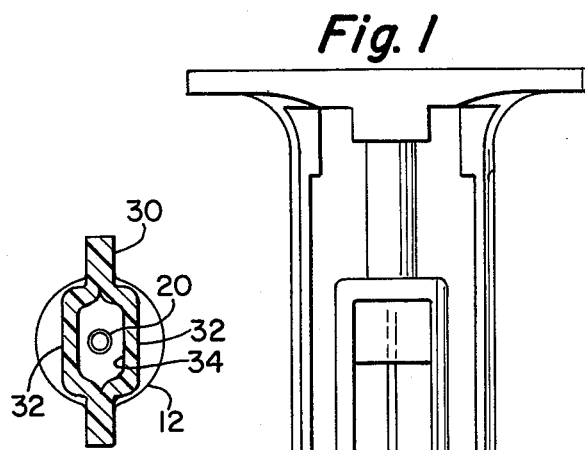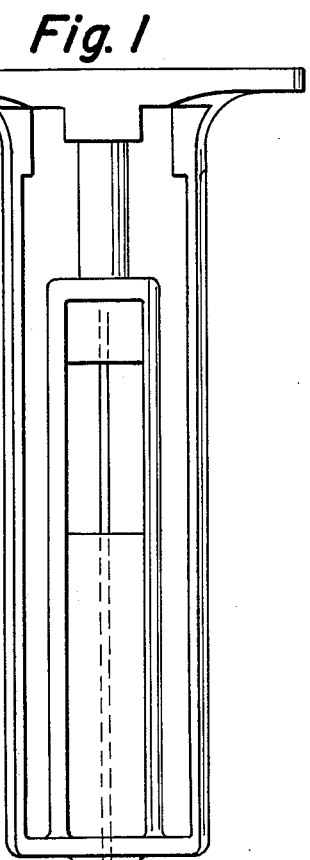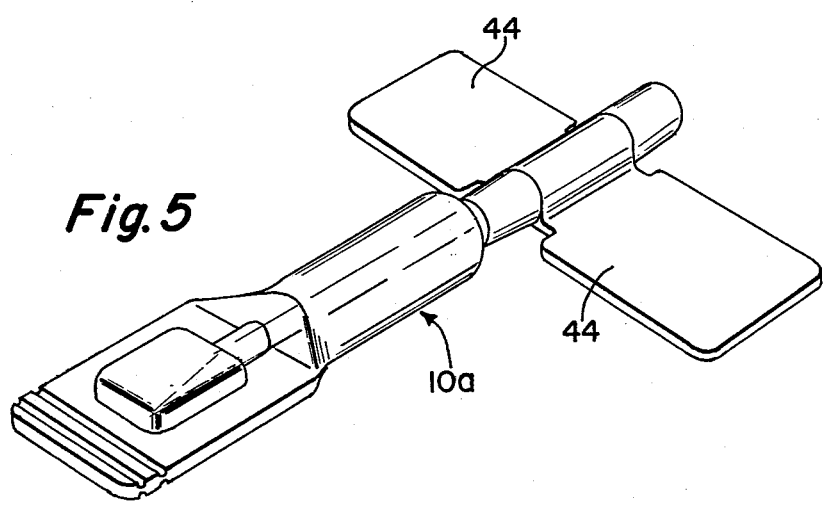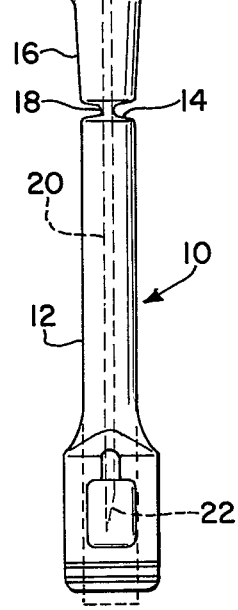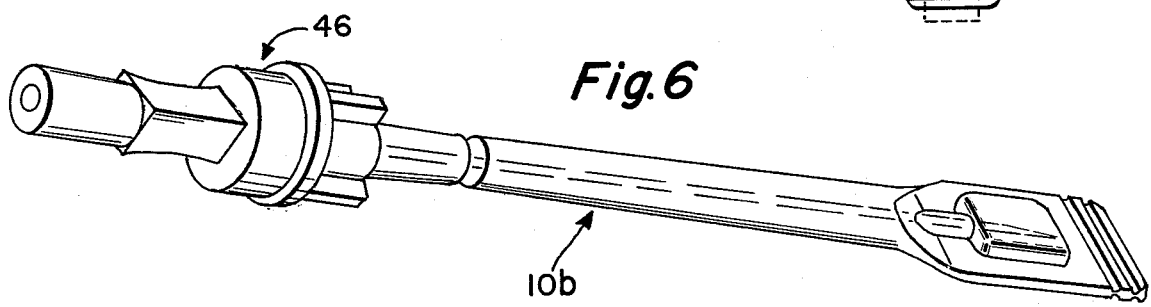

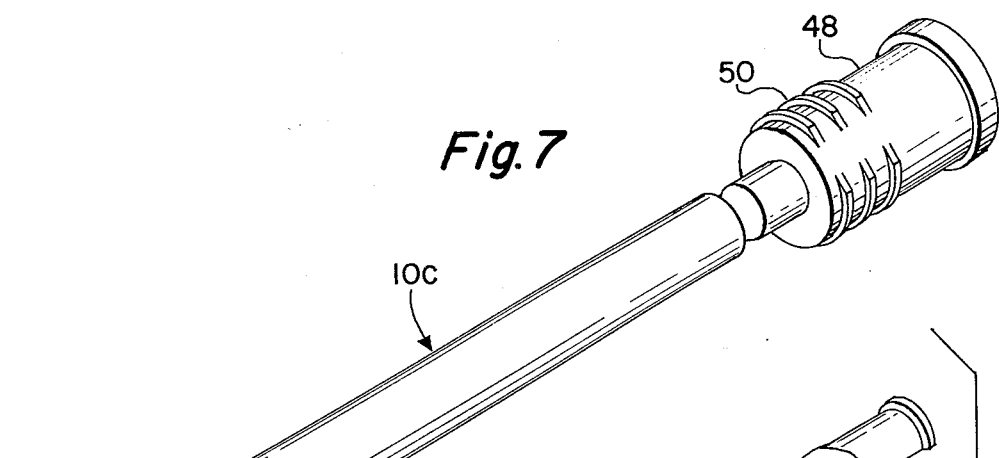
Fig. 7
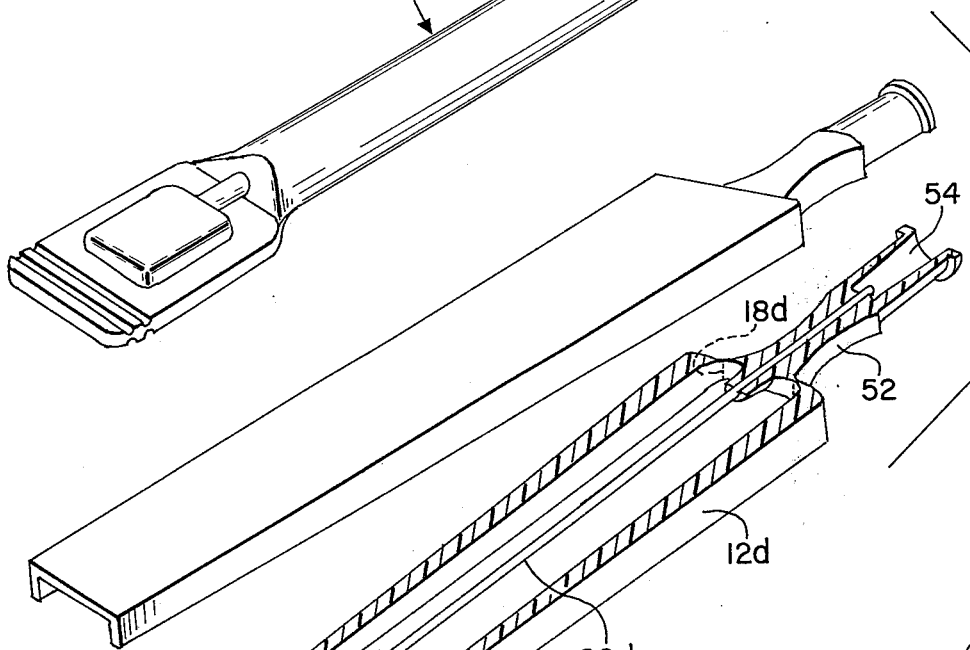
Fig. 8
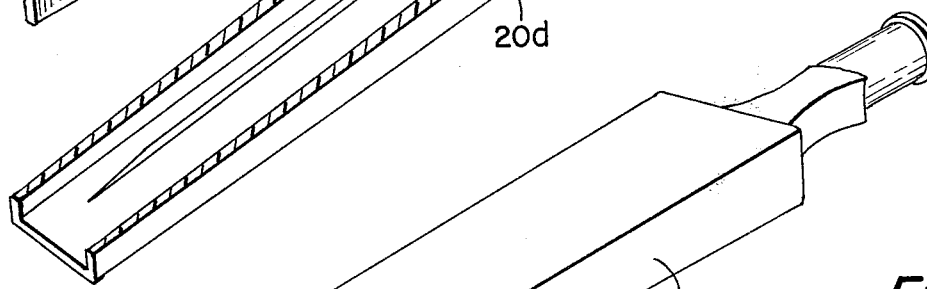
Fig. 9
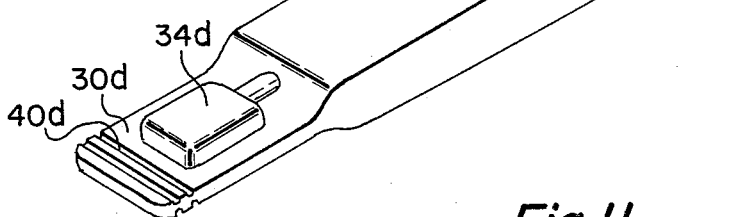
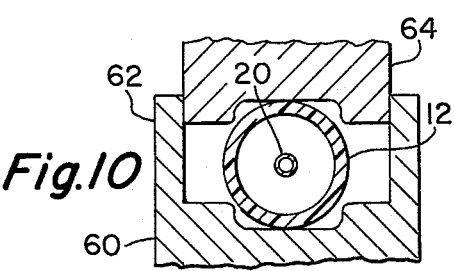
Fig. 10
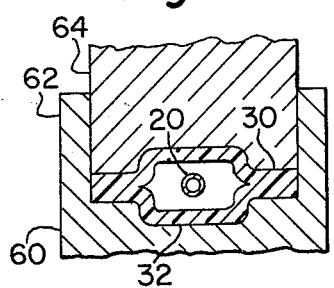
Fig. 11
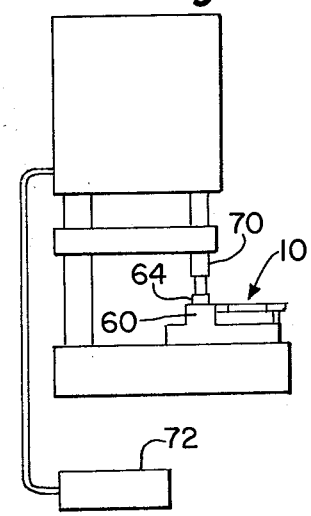
Fig. 12

CANNULA COVER

BACKGROUND OF THE INVENTION

Various forms of cannula or needle covers have been employed to this date. Some of these involve simple closed or open end rubber tubes encircling the cannula; sealed glass tubes which are breakable; molded tubular elements encircling the cannula and extending beyond the free end and molded plastic tubes which are integrally joined to the supporting structure or hub surrounding the anterior end of said cannula. While certain of these are adequate for their particular needs, they fail to cover all of the functions required under certain circumstances, namely, the maintenance of aseptic conditions surrounding a cannula that is to be utilized for intravenous injections, intermuscular injections or any other subcutaneous injections administered to patients. Additionally, when such covers are utilized with cannulas attached to a medicament source, it is virtually impossible to insure that they have not been tampered with, i.e., the contents of the medicament container withdrawn and replaced by a secondary undesirable material. Attempts have been made to seal the ends of such cannula covers or to embed the sharpened distal end of the cannula in soft material. One of the major problems in the previous attempts has been the presence of particles of the cover material being found in the lumen of the cannula which either blocks the flow of medicament or, alternatively, can be devastatingly injurious to the patient's health if such particles become introduced into the bloodstream after penetration by the sharpened end of the cannula.

SUMMARY OF THE INVENTION

An object of the present invention is to provide a cover which hermetically seals the sharpened distal end of a cannula by providing a bubble-like structure spaced from the distal end which will protect the ground beveled edges which provide the sharpened end.

A further object of the invention is to provide a hermetically sealed cover in which melted plastic is not allowed to flow into the inner diameter or lumen of the cannula and freeze, which, alternatively, prevents drug flow or provides particles in the lumen which can be introduced into a patient's bloodstream.

Another object of the present invention is to provide an economical means for sealing a cannula and which offers a flat surface which can be used for leverage to break the cover away from engagement with the cannula to expose the cannula for administration of drugs to a patient.

An additional object is to provide a cover which can be frangibly connected to the main supporting body or hub surrounding the anterior end of a cannula and when sealed by the method of this invention provides a tamper-proof means for preventing undesired access to the medicament container.

Other objects of the present invention will be apparent to those skilled in the art when the drawing is considered in the light of the detailed specification.

BRIEF DESCRIPTION OF THE DRAWINGS

FIG. 1 is an elevational view of an infusor using a cover of the type contemplated by the present invention;

FIG. 2 is an enlarged partial elevational view in inverted position from FIG. 1 of the specific detail of the end of the cover contemplated by this invention;

FIG. 3 is a side view of the device shown in FIG. 2;

FIG. 4 is a partial sectional view taken along line 4 — 4 of FIG. 3;

FIG. 5 is a perspective view of a scalp vein needle utilizing a cover of the present invention;

FIG. 6 is a blood donor needle utilizing a cover contemplated by the present invention;

FIG. 7 is a needle having a hub with split threads thereon for use with a unit-dose medicament system utilizing a cover of the present invention;

FIG. 8 is an exploded view in partial section of a cover having a generally rectangular configuration in cross section;

FIG. 9 is the cover shown in FIG. 8 in assembled relation with a seal of the type contemplated by the present invention;

FIG. 10 is a partial elevational view in section of an anvil and die of the general type used to form the sealed end of this cover before flattening of the cover;

FIG. 11 is a similar view to FIG. 10 with the anvil and die in the holding position after forming and welding; and FIG. 12 is a schematic diagram of a typical machine for accomplishing the forming of the sealed end.

DETAILED SPECIFICATION

Referring now to the drawings wherein similar numerals are used to designate similar parts, a cover 10 for an elongated cannula, having a sharpened distal end, generally includes a tubular body 12 provided with a closed end wall 14 having a central aperture encircling and sealing around the body of the cannula 20. In the device shown in FIG. 1 the end wall 14 and its central aperture are interconnected to the hub 16 of the body by means of a frangible section 18. The opposite end of the tube 12 is open and extends beyond the sharpened distal end 22 of the needle 20. In the present embodiment the cover 12 is generally cylindrical in configuration. This is flattened, as will be described hereinafter, by appropriate means to form a flattened end 30 having two bubblelike pocket structures 32 extending outwardly from opposite sides of the flattened portion 30 to form a chamber 34 surrounding but spaced from the bevel ground edges of the distal end.

The flattened portion 30 also includes a semicylindrical portion 36 which embraces the cannula adjacent to but spaced from the sharpened end in sealing relationship thereto. This semicircular portion blends into the beveled portion 38 which assists in the transition from the tubular cylindrical form of the cover 12 into the flattened sealed end 30. The tube 12 in its initial condition is shown in phantom in FIG. 2 and FIG. 3 to illustrate the condition of the cover 12 prior to formation of the sealed end. Extending transversely to the end of the flattened portion are one or more grooves 40 which serve as high energy source receivers to insure that the free end of the cover 12 is hermetically sealed, this is a safeguard in the event of failure of the flattened portions 30 from being totally sealed at the perimeter around the bubble-like pocket structures 32.

As can be appreciated by those skilled in the art, the beveled ground ends of a cannula used for intravenous or other forms of injection are extremely sensitive items and the least amount of touching will dull the edges which have been sharpened by grinding. In the present invention, the provision of the chamber 34 spaced in all directions from the sharpened distal end 22 of the cannula 20 insures that the end 22 is protected from dulling. Secondly, the presence of the chamber 34 with its spaced walls and inner surfaces insures that no plastic materials will be allowed to flow into the lumen of the cannula and freeze thereby preventing drug flow through the cannula. Further, it insures that no particles of plastic will become lodged in the lumen of the cannula 20 which could be inadvertently injected into the vein of a patient to whom drugs are being administered and thereby create a deleterious situation. By sealing the chamber 34 with the semicylindrical portions 36 an additional benefit is realized, namely, that if an infusor of the type shown in FIG. 2 is attached to a drug source which is inadvertently activated, then only a limited amount of drug can be expelled to the limits of the volume of chamber 34. In the prior art the entire elongated cover could be filled and hence the patient would not receive the full doseage desired.

When the cover 12 is frangibly connected as at 18 to the main body or hub 16, the hermetically sealing of the point 22 insures that when the cannula 20 communicates with a drug source positive evidence is available as to when the device is tampered with and possible removal of the original drug and replacement by an undesirable substance.

The cover embodiment just described is preferably injection molded of polypropylene, a substance which is acceptable when it comes in contact with drugs.

Referring to FIGS. 10 through 12, one method of sealing the end of the cover is through the use of a mating anvil 60 having vertical side walls 62 and a compressing die 64 that is integral with the horn 70 of an ultrasonic energy source with the facing surface of the anvil and die being mirror images of the flattened end 30 and bubble-like chamber 34. An energy exemplary source 72 would have a 350 watt energy level while producing substantially 20,000 cycles per second. The cover, cannula and body are suitably supported by a jig and fixture with the end of cover 12 being accurately positioned between anvil 60 and die 64. Suitable means, not shown such as a hydraulic or pneumatic cylinder, moves the horn 70 with the die 64 carried thereon toward the anvil 60 to compress the round tube cover 12 into the flattened condition. A welding cycle of 0.3 to 0.5 seconds is used with the energy source being activated for a fraction of the cycle before the tube is totally compressed. This ultrasonic energy transmitted through the die 64 causes the contacting material to fuse or melt at the interfaces formed on the interior of the cover. The natural tendency of the plastic material, sometimes referred to as "memory" is to want to remain in its original molded form which causes the tube 12 to readily form into the cavities of anvil 60 and die 64 to form the bubble-like structure 32. When the energy source is turned off, the welded cover is maintained for a holding cycle of generally 1.0 to 1.5 seconds to insure total cooling and bonding of the plastic material, with the die 64 being maintained in the general position shown in FIG. 11.

While the energy source is generally acceptable to seal the flattened portion 30, the anvil 60 and die 64 each have one or more transverse ribs which act as energy concentrators which produce the grooves 40 in the end area of the flattened portion 30. In ultrasonic techniques these ribs will concentrate the energy and insure sealing of the end of the cover 12.

While ultrasonics have been discussed hereinabove as the energy source for welding the end of the cover, it will be recognized that R.F. circuits or controlled heat sources may also be utilized, either of the induction or direct resistance heater element types.

While a cover of the type described hereinabove has been illustrated as being attached to an infusor, in FIG. 1, it should be recognized that the techniques are applicable to other devices which will utilize a sharpened cannula. As an illustrative example, FIG. 5 shows a cover 10a, of the type contemplated by this invention, as applied to and used with a scalp vein needle having a pair of laterally extending flaps 44 generally utilized to accept tape, not shown, for maintaining the cannula relative to the patient's epidermis. FIG. 6 shows a cover 10b, of the type discussed hereinabove, as it is applied to a blood donor needle 46. FIG. 7 shows a cover 10c of a similar construction attached to a cannula having a hub 48 provided with annular screw threads 50 of the type adapted to be utilized with a holder for acceptance of unit-dose vials.

FIG. 8 is an exploded perspective view showing a cannula 20d provided with a hub 52 with a leur female type fitting 54. In this device, which is shown in two halves for purposes of illustration, the cover 12d is generally flat or rectangular in cross section and connected to the hub 52 by frangible connections 18d. FIG. 9 illustrates such a device with the cover 20d provided with a flattened sealed portion 30d, a bubble-like chamber 34d and sealing grooves 40d. The function of this embodiment is to show the applicability to shapes other than the cylindrical form shown in the first embodiment.

It should be recognized that a cover of the type disclosed by the present invention could similarly be utilized on double-ended needles having a central hub with a separate cover extending outwardly and frangibly connected to the hub to provide the aseptic hermetical sealing of the cannula ends. Additionally, other forms of cannula applications that would require the use of a hermetically sealed tamper-proof closure will be apparent to those skilled in the art.

I claim:

1. A cover for an elongated cannula having a sharpened distal end, said cover including an elongated tubular member concentrically disposed around a substantial portion of the length of said cannula with one end of said cover engaging said cannula in encircling arrangement intermediate its length, the second end of said cover extending beyond the sharpened distal end of said cannula and providing a sealed chamber, the walls of said chamber being formed by one or more bubble-like pockets in said cover spaced from the sharpened distal end of said cannula and said one or more pockets being completely sealed around the periphery of said chamber with one wall, intermediate the extremities of said cover, intimately engaging and conforming to said cannula at a point adjacent to but spaced from said sharpened tip.

2. A cover of the type claimed in claim 1 wherein said one end is frangibly connected to a body supporting the cannula at a point spaced from said distal end.

3. A cover of the type claimed in claim 1 wherein said cover is initially an open ended cylinder and is deformed to a flattened configuration extending beyond the distal end of said cannula with a domed pocket being provided in the central area of said flattened portion with the interior of said chamber formed by said pocket being spaced from the sharpened distal end of said cannula.

4. A cover of the type claimed in claim 3 wherein said flattened portion grips and is complimentary to said cannula at a point adjacent to but spaced from the sharpened end thereof, said flattened portion serving as a break-away gripping means for slideably removing said cover from said cannula.

5. A cover of the type claimed in claim 4 wherein said cover at its one end is frangibly connected to a secondary body encircling said cannula whereby said cannula is sealed from said body throughout the balance of its length to said sharpened distal end.

6. A cannula assembly including a cannula having an anterior end and a sharpened distal end, supporting body means encircling and engaging said cannula adjacent its anterior end and providing access to the open anterior end of said cannula, tubular cover means encircling said cannula from a point intermediate its length to a point beyond the sharpened distal end of said cannula, said latter end of said cover being deformed from its initial tubular configuration to a flattened configuration encircling and sealing said cannula at a point adjacent to but spaced from said sharpened distal end and providing a domed pocket encircling but spaced from said sharpened distal end of said cannula, said flattened portion being sealed completely around the periphery of said pocket and intimately engaging and conforming to said cannula for a portion thereof adjacent to but spaced from said sharpening distal end.

7. A device of the type claimed in claim 6 wherein said cover is generally cylindrical in configuration.

8. A device of the type claimed in claim 6 wherein said pocket includes a generally noncircular bubble extending outwardly from opposite sides of said flattened portion.

9. A device of the type claimed in claim 8 wherein the free end of said flattened portion is reinforced by a transverse rib.

10. A device of the type claimed in claim 6 wherein the first end of said cover is frangibly connected to the supporting body encircling the anterior end of said cannula.

11. A device of the type claimed in claim 6 wherein said body portion encircling the anterior end of said cannula is provided with means for connection to a tubular means for communication with the open anterior end of said cannula.

12. A device of the type claimed in claim 11 wherein said body includes at least one laterally extending wing element for assisting in the retention of the cannula relative to a patient's epidermis.

13. A device of the type claimed in claim 11 wherein said body includes screw threaded means for association with a secondary element.

14. A device of the type claimed in claim 11 wherein said body includes finger gripping means and a tapered leur fitting for association with a secondary element.

15. A device of the type claimed in claim 6 wherein said tubular cover is substantially noncircular in cross-sectional configuration and provided with a flattened end adjacent the distal end of said cannula hermetically sealing said end and providing a bubble-like pocket spaced from said sharpened distal end of said cannula.

16. A device of the type claimed in claim 15 wherein said cover is frangibly connected to said body adjacent the anterior end of said cannula.

17. A device of the type claimed in claim 6 wherein said flattened end portion includes a rectangular bubble-like pocket extending outwardly from opposite sides in spaced relation to said sharpened distal end, said flattened portion in its central longitudinal axis surrounding and sealingly engaging the cannula adjacent to but spaced from said sharpened distal end, at least one transverse groove sealing the free end of said flattened portion as secondary sealing to enhance the sealing of said flattened portion formed by the interior walls of said tubular member, when flattened, that surround said bubble-like pocket.

* * * * *